(12) United States Patent
Lee et al.

(10) Patent No.: US 8,013,366 B2
(45) Date of Patent: Sep. 6, 2011

(54) BIOSENSOR USING NANOSCALE MATERIAL AS TRANSISTOR CHANNEL AND METHOD OF FABRICATING THE SAME

(75) Inventors: Moon-Sook Lee, Seoul (KR);
Byeong-Ok Cho, Seoul (KR);
Man-Hyoung Ryoo, Hwaseong-si (KR);
Takahiro Yasue, Suwon-si (KR);
Jung-Hwan Hah, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 137 days.

(21) Appl. No.: 12/232,243

(22) Filed: Sep. 12, 2008

(65) Prior Publication Data

US 2009/0085072 A1    Apr. 2, 2009

(30) Foreign Application Priority Data

Sep. 17, 2007 (KR) .................. 10-2007-0094290

(51) Int. Cl.
*G01N 27/403* (2006.01)
*H01L 21/00* (2006.01)

(52) U.S. Cl. ............ 257/253; 257/414; 257/E29.255; 257/E21.575; 257/E21.568; 438/49; 438/458

(58) Field of Classification Search .......... 438/49, 438/48, 458; 257/253, E21.158, E29.255, 257/E21.568, E21.575, E29.245, E21.159, 257/E21.4, E21.29; 977/920, 938, 940, 941, 977/947, 953, 957, 958, 943
See application file for complete search history.

(56) References Cited

U.S. PATENT DOCUMENTS

| | | | | |
|---|---|---|---|---|
| 5,605,662 | A * | 2/1997 | Heller et al. | 422/68.1 |
| 6,870,235 | B2 | 3/2005 | Abstreiter et al. | |
| 7,084,507 | B2 * | 8/2006 | Awano | 257/773 |
| 7,348,675 | B2 * | 3/2008 | Dubin et al. | 257/774 |
| 2003/0215865 | A1 * | 11/2003 | Mayer et al. | 435/6 |
| 2004/0023413 | A1 * | 2/2004 | Opalsky | 436/518 |
| 2004/0253805 | A1 | 12/2004 | Dubin et al. | |
| 2006/0240588 | A1 * | 10/2006 | Conley et al. | 438/49 |

(Continued)

FOREIGN PATENT DOCUMENTS

EP    1 473 767 A2    11/2004
(Continued)

OTHER PUBLICATIONS

Office Action for corresponding GB Appl. No. 0817058.1, dated Dec. 24, 2008.

*Primary Examiner* — Matthew C Landau
*Assistant Examiner* — Latanya Crawford
(74) *Attorney, Agent, or Firm* — Harness, Dickey & Pierce, PLC

(57) ABSTRACT

Example embodiments relate to a biosensor using a nanoscale material as a channel of a transistor and a method of fabricating the same. A biosensor according to example embodiments may include a plurality of insulating films. A first signal line and a second signal line may be interposed between the plurality of insulating films. A semiconductor nanostructure may be disposed on the plurality of insulating films, the semiconductor nanostructure having a first side electrically connected to the first signal line and a second side electrically connected to the second signal line. A plurality of probes may be coupled to the semiconductor nanostructure. A biosensor according to example embodiments may have a reduced analysis time.

21 Claims, 12 Drawing Sheets

U.S. PATENT DOCUMENTS

| | | |
|---|---|---|
| 2007/0158679 A1 | 7/2007 | Li et al. |
| 2007/0292855 A1* | 12/2007 | Dubin et al. .................. 435/6 |
| 2008/0079041 A1 | 4/2008 | Suk et al. |
| 2008/0214409 A1* | 9/2008 | Kim et al. .................. 506/15 |
| 2008/0283875 A1 | 11/2008 | Mukasa et al. |
| 2008/0319298 A1* | 12/2008 | Huys et al. .................. 600/377 |
| 2009/0075414 A1* | 3/2009 | Lee et al. .................. 438/49 |
| 2009/0114901 A1* | 5/2009 | Xie et al. .................. 257/14 |
| 2009/0127589 A1* | 5/2009 | Rothberg et al. ............. 257/253 |
| 2009/0153130 A1* | 6/2009 | Shim et al. .................. 324/72 |
| 2009/0298231 A1* | 12/2009 | Carothers .................. 438/113 |
| 2009/0302394 A1* | 12/2009 | Fujita .................. 257/369 |
| 2010/0052080 A1* | 3/2010 | Garcia Tello et al. ........ 257/414 |
| 2010/0055699 A1* | 3/2010 | Kahya .................. 435/6 |
| 2010/0109645 A1* | 5/2010 | Park et al. .................. 324/123 R |
| 2010/0248209 A1* | 9/2010 | Datta et al. .................. 435/5 |

FOREIGN PATENT DOCUMENTS

| | | |
|---|---|---|
| EP | 1 666 873 A1 | 6/2006 |
| JP | 2006-220513 | 8/2006 |
| JP | 2006-258661 | 9/2006 |
| KR | 10-0702531 | 3/2007 |
| WO | WO 2005/078819 | 8/2005 |
| WO | WO 2007/109228 | 9/2007 |

* cited by examiner

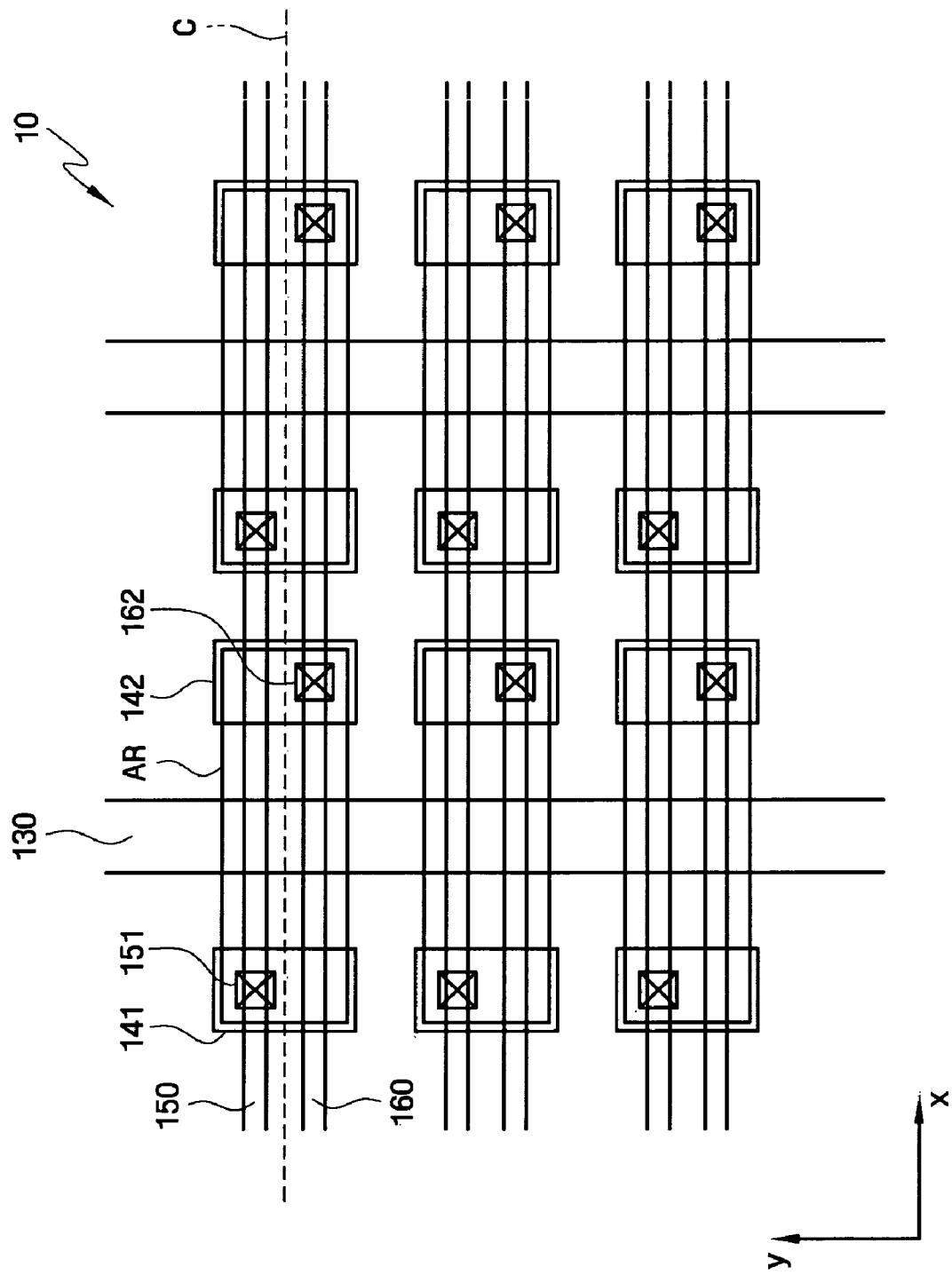

BIOSENSOR USING NANOSCALE MATERIAL AS TRANSISTOR CHANNEL AND METHOD OF FABRICATING THE SAME

PRIORITY STATEMENT

The present application claims priority under 35 U.S.C. §119 to Korean Patent Application No. 10-2007-0094290, filed on Sep. 17, 2007 in the Korean Intellectual Property Office (KIPO), the entire contents of which are incorporated herein by reference.

BACKGROUND

1. Technical Field

Example embodiments of the present application relate to biosensors and methods of fabricating biosensors.

2. Description of the Related Art

Biosensors are used to analyze bio-samples by allowing the probes of a biosensor to interact with a bio-sample and observing which reactions occurred between the bio-sample and the probes. For instance, a fluorescent analysis may be used to analyze a bio-sample. In such an analysis, probes having different base sequences are fixed on corresponding cells of a biosensor by base sequence type, and a bio-sample marked with a fluorescent material is allowed to interact with the probes. Consequently, the fluorescent material may remain on some of the cells as a result of the coupling of the bio-sample with certain probes via hybridization. The cells with the fluorescent material are identified with a scanner. Accordingly, the substances constituting the bio-sample are determined based on the identified cells with the fluorescent material.

However, fluorescent analysis of a bio-sample takes a relatively long period of time because of the steps involved, including marking the bio-sample with fluorescent material and performing the scanning process. Furthermore, accurately collecting and analyzing the light emitted from the fluorescent material is not easy.

SUMMARY

A biosensor according to example embodiments may include a plurality of insulating films. A first signal line and a second signal line may be interposed between the plurality of insulating films. A semiconductor nanostructure may be disposed on the plurality of insulating films, the semiconductor nanostructure having a first side electrically connected to the first signal line and a second side electrically connected to the second signal line. A plurality of probes may be coupled to the semiconductor nanostructure.

A method of fabricating a biosensor according to example embodiments may include disposing a semiconductor nanostructure on a substrate. A plurality of insulating films, a first signal line, and a second signal line may be formed on the semiconductor nanostructure, the first signal line being electrically connected to a first side of the semiconductor nanostructure and the second signal line being electrically connected to a second side of the semiconductor nanostructure. The semiconductor nanostructure may be exposed by removing the substrate. A plurality of probes may be coupled to the semiconductor nanostructure.

BRIEF DESCRIPTION OF THE DRAWINGS

The above and other features of example embodiments may become more apparent upon review of the attached drawings, wherein:

FIG. 1 is a schematic layout of a biosensor according to example embodiments;

DETAILED DESCRIPTION OF EXAMPLE EMBODIMENTS

Figure 2A:
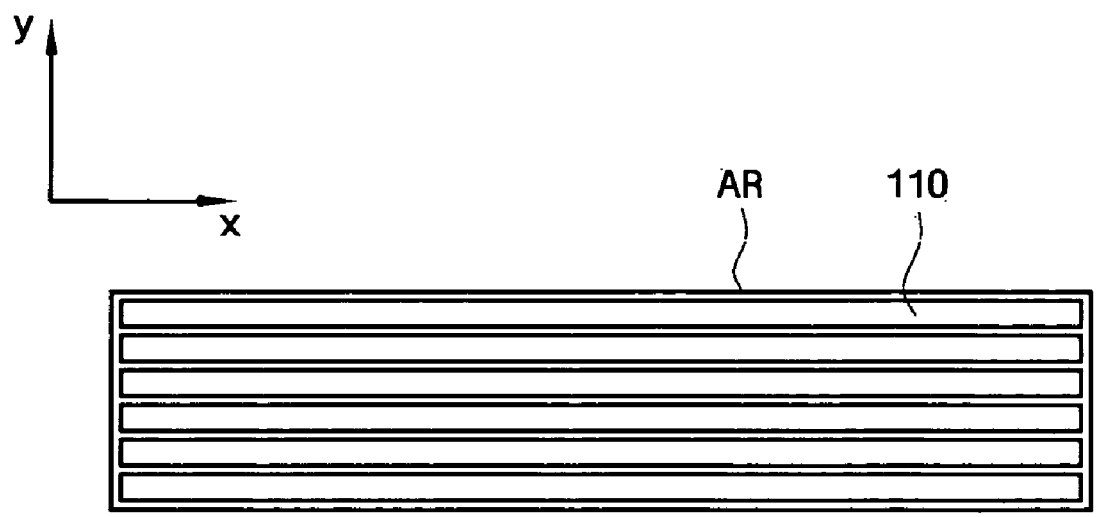
FIGS. 2A and 2B are schematic plan views of semiconductor nanostructures for the active area of FIG. 1.

Advantages and features of example embodiments may be better appreciated upon review of the detailed description in conjunction with the accompanying drawings. However, it should be noted that example embodiments may be embodied in many different forms and should not be construed as being limited to the examples herein.

It will be understood that when an element or layer is referred to as being "on", "connected to", "coupled to", or "covering" another element or layer, it may be directly on, connected to, coupled to, or covering the other element or layer or intervening elements or layers may be present. In contrast, when an element is referred to as being "directly on," "directly connected to" or "directly coupled to" another element or layer, there are no intervening elements or layers present. Like numbers refer to like elements throughout the specification. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, e.g., "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Biosensors according to example embodiments may be used to analyze biomolecules contained in biological samples for purposes of performing gene expression profiling, genotyping through detection of mutation/polymorphism (e.g., Single-Nucleotide Polymorphism (SNP)), protein/peptide assays, potential drug screening, development and preparation of novel drugs. Biosensors may employ probes which are tailored to the type of biological sample being analyzed. Examples of biosensor probes may include DNA probes, protein probes (e.g., antibody/antigen, bacteriorhodopsin), bacterial probes, and neuron probes. A biosensor fabricated in the form of a chip may also be referred to as a biochip. For example, a biosensor may be referred to as a DNA chip, a protein chip, a cellular chip, or a neuron chip, depending on the type of probe used.

Biosensors according to example embodiments may contain oligomer probes. Consequently, the number of monomers contained in the oligomer probe is at the oligomer level. As used herein, the term "oligomer" may be a relatively low-molecular weight polymer molecule having two or more covalently-bound monomers. The molecular weight of the monomer may be about 1,000 or less, although example embodiments are not limited thereto. The oligomer may include about 2-500 monomers, although example embodiments are not limited thereto. For instance, the oligomer may include about 5-300 monomers (e.g., about 5-100 monomers). The monomers may vary depending on the type of biological sample being analyzed. For example, the monomers may be nucleosides, nucleotides, amino acids, and/or peptides, depending on the probe type.

As used herein, the terms "nucleosides" and "nucleotides" may include not only known purine and pyrimidine bases, but also methylated purines or pyrimidines, acylated purines or pyrimidines, and the like. Furthermore, the "nucleosides" and "nucleotides" may include not only known (deoxy)ribose, but also modified sugars which contain halogen and/or aliphatic substitutions for at least one hydroxyl group or modified sugars functionalized with ether, amine, or the like. As used herein, the term "amino acids" may refer not only to naturally occurring, L-, D-, and nonchiral amino acids, but also to modified amino acids, amino acid analogs, and the like. As used herein, the term "peptides" may refer to compounds produced by an amide bond between the carboxyl group of one amino acid and the amino group of another amino acid.

For purposes of illustration, the probes used in example embodiments may be DNA probes, although other types of probes may be used. The DNA probes may be oligomer probes covalently-bound with about 5-30 nucleotide monomers. Hereinafter, example embodiments will be described in further detail with reference to the attached drawings. The dimensions of various aspects of the drawings may have been exaggerated for purposes of clarity.

Referring to FIG. 1, a biosensor 10 according to example embodiments may include at least one active area AR, at least one first signal line 150, and at least one second signal line 160. The active area AR may be occupied by a semiconductor nanostructure. For instance, the semiconductor nanostructure may be disposed only in the active area AR. The semiconductor nanostructure may be formed of semiconductor nanoscale substances or materials. The semiconductor nanoscale substances may include Si, ZnO, GaN, Ge, InAs, GaAs, C, or combinations thereof. For instance, the semiconductor nanostructure may be a multi-walled nanostructure having a core and at least one shell surrounding the core. An example of a multi-walled nanostructure may be a double-wall nanostructure having a Ge core and a Si shell.

The nanostructure may be a structure having a nano-sized diameter or a nano-sized thickness. The nano-sized diameter or nano-sized thickness may be several nanometers to several tens of nanometers. The nanostructure may include nanowires, nanotubes, and/or nanoparticles. The active area AR may be rectangular, substantially rectangular with rounded corners, or oval in shape. Although the shape of the active area AR is not limited to above-mentioned shapes, the active area AR may have a semiconductor-type conductivity along its major axis (e.g., X direction in FIG. 1). The semiconductor-type conductivity may enable the active area AR to function as a channel of a transistor that conducts electricity depending on applied voltage or current conditions.

Figure 2B:
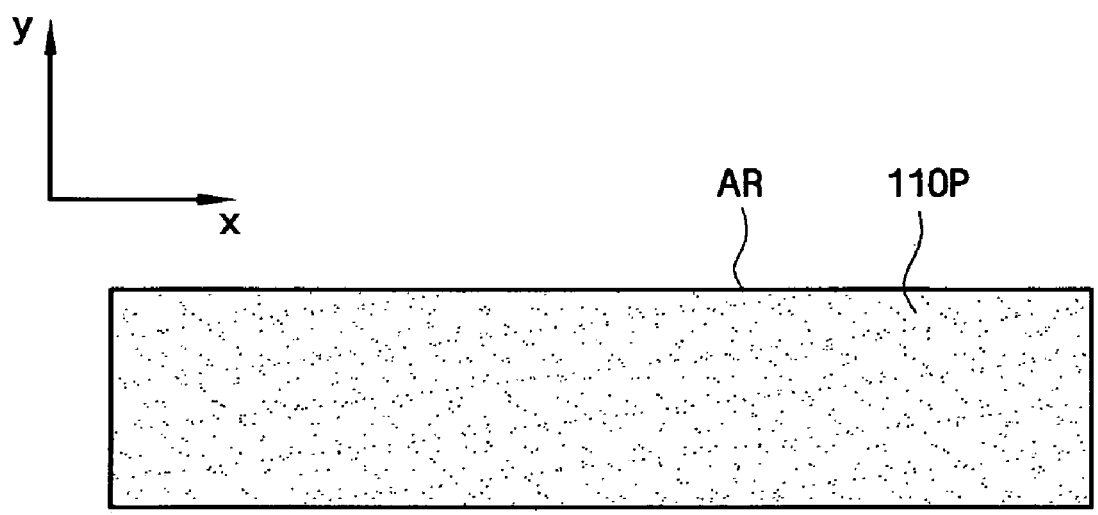

Referring to FIG. 2A, a plurality of semiconductor nanowires 110 (e.g., semiconductor nanotubes) may be disposed in parallel along the X direction of the active area AR. Consequently, the active area AR may have one-dimensional semiconductor-type conductivity in the X direction. Referring to FIG. 2B, when semiconductor nanoparticles 10p are clustered in the active area AR, the active area AR may have a two-dimensional semiconductor-type conductivity.

Referring to FIG. 1, the first signal line 150 and the second signal line 160 may extend in one or more directions. For example, the first signal line 150 and second signal line 160 may traverse the active area AR and extend in parallel along the X direction. To avoid a short circuit between the first and second signal lines 150 and 160, it may be beneficial for the first and second signal lines 150 and 160 to not overlap each other. The first signal line 150 may be a source line that provides a channel (e.g., the semiconductor nanostructure) with source current, and the second signal line 160 may be a drain line that detects drain current.

The first signal line 150 may be electrically connected to a first side of the semiconductor nanostructure, and the second signal line 160 may be electrically connected to a second side of the semiconductor nanostructure. When the biosensor 10 includes a plurality of active areas AR disposed along the X direction, the first signal line 150 may be electrically connected to the first sides of the semiconductor nanostructures placed in each of the active areas AR. Similarly, the second signal line 160 may be electrically connected to the second sides of the semiconductor nanostructures placed in each of the active areas AR.

The first signal line 150 may be electrically connected to the semiconductor nanostructure though a first contact 151. The second signal line 160 may be electrically connected to the semiconductor nanostructure through a second contact 162. When each semiconductor nanostructure includes a plurality of nanowires 110 (e.g., nanotubes) as shown in FIG. 2A, the semiconductor nanostructure may have a one-dimensional semiconductor-type conductivity. As a result, the semiconductor nanostructure may exhibit semiconductor-type conductivity in the X direction, but with little or no conductivity in the Y direction.

The first and second signal lines 150 and 160 may pass over the same active area AR at the same time. To ensure that the first contact 151 contacts only the first signal line 150 and that the second contact 162 contacts only the second signal line 160, the widths of the first and second signal lines 150 and 160 and the widths of the first and second contacts 151 and 162 may be restricted in the Y direction. For instance, the width and position of the first signal line 150 and the first contact 151 may be restricted to the upper half of the active area AR above the center line C. Conversely, the width and position of the second signal line 160 and the second contact 162 may be restricted to the lower half of the active area AR below the center line C.

When a plurality of semiconductor nanowires are disposed in parallel in the X direction, electrically connecting the semiconductor nanowires to the first signal line 150 through the first contact 151 and the semiconductor nanowires to the second signal line 160 through the second contact 162 may be difficult. The electrical connection between the first and second signal lines 150 and 160 and the semiconductor nanowires may depend on the semiconductor-type conductivity of the nanostructure in the Y direction. However, as described above, there may be relatively little or no conductivity in the Y direction when the nanowires are arranged in parallel in the X direction. Accordingly, establishing an electrical connection between the parallel nanowires and the parallel first and second signal lines 150 and 160 may be difficult.

To ensure sufficient conductivity in the Y direction on the first and second sides of the active area AR where the first and second contacts 151 and 162 are respectively connected, the first and second sides of the active area AR may be provided with a first contact pad 141 and a second contact pad 142, respectively. The first and second contact pad 141 and 142 may be wide enough to cover the width of the active area AR in the Y direction. For example, the first and second contact pads 141 and 142 may be about equal to or larger than the width of the active area AR in the Y direction so as to cover the first and second sides, respectively, of the active area AR. When the first and second contact pads 141 and 142 are rectangular shaped, they may cover the necessary areas and obtain process margins between the probe cell and neighboring probe cells.

As a result, the electrical connection between the first signal line 150 and the first side of the semiconductor nanostructure may be established through the first contact 151 and the first contact pad 141. Although the width (or diameter) of the first contact 151 may be restricted, the first signal line 150 may still be electrically connected to every semiconductor nanowire in the first side of the active area AR by virtue of the first contact pad 141. Thus, a relatively secure electric connection between the first signal line 150 and the semiconductor nanostructure through the first contact 151 may be achieved. Similarly, the electric connection between the second signal line 160 and the second side of the semiconductor nanostructure may be established through the second contact 162 and the second contact pad 142, and the same implementation applied to the first signal line 150 may be applied to the second signal line 160.

On the other hand, when the active area AR has clustered nanoparticles disposed thereon, the active area AR may have two-dimensional semiconductor-type conductivity. As a result, the first and second contact pads 141 and 142 may not be necessary. Nevertheless, it may still be beneficial to apply the first and second contact pads 141 and 142 to reduce resistance and to ensure a more secure connection with first and second contacts 151 and 162.

Although not illustrated in FIG. 1, a plurality of probes may be coupled to the semiconductor nanostructure in each active area AR. The probes may be coupled to the semiconductor nanostructure directly or indirectly by means of activation layers (e.g., coating film 120 in FIGS. 11-13 or surface activation layer 191 in FIG. 15) and/or linkers (e.g., 201 in FIGS. 11-16) in the active area AR. Different probes (e.g., probes with different base sequences) may be coupled in different active areas AR, such that one active area AR may have one type of probe while another active area AR may have another type of probe. Each active area AR may form a probe cell. The number of active areas AR may represent the number of probe cells.

When a bio-sample becomes coupled to a probe by virtue of a reaction (e.g., hybridization), a difference in the surface charge density of the semiconductor nanostructure may occur. As a result, the conductance of the semiconductor nanostructure may change. Thus, the presence of the bio-sample coupled to the probe may determine whether the semiconductor nanostructure has a certain conductance. This difference in conductance may be detected by the first and second signal lines 150 and 160, which are connected to the first and second sides, respectively, of the semiconductor nanostructure. Consequently, a relatively reliable analysis of a bio-sample by the biosensor 10 may be achieved without having to perform additional processes (e.g., fluorescent analysis). Additionally, the analysis time of the bio-sample may be reduced.

A gate line 130 may be optionally included in the active area AR. The gate line 130 may pass through the center of the active area AR and extend in the Y direction. The gate line 130, the first signal line 150 (e.g., source line), the second signal line 160 (e.g., drain line), and the semiconductor nanostructure may form a transistor. A threshold voltage provided by the gate line 130 may enhance the accuracy and sensitivity of the detection of a reaction. When a plurality of active areas AR are arranged in a matrix, the gate line 130 may select one row (or column) of active areas AR and assist in the analysis of the selected active areas AR. However, as noted above, the gate line 130 may be omitted.

A cross-sectional structure of a biosensor having the above-described layout will be described below. Additionally, nanowires formed of a semiconductor nanoscale material (e.g. silicon (Si)) are described below as an example of a semiconductor nanostructure. However, it should be understood that other semiconductor nanostructures may be used instead of the nanowires. The biosensor according to example embodiments will also be described in conjunction with the fabricating method thereof. The cross-sectional views of the biosensor may be better appreciated with additional reference to FIG. 1.

Figure 3:
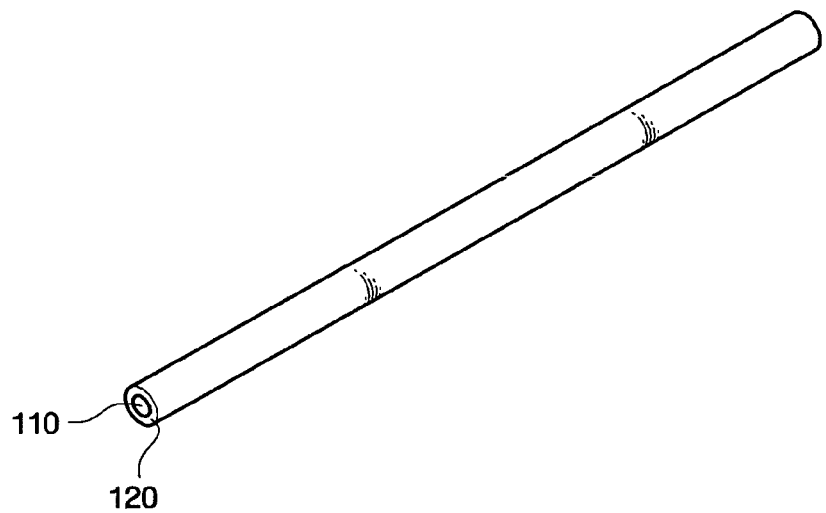
FIG. 3 is a perspective view of a nanowire of the semiconductor nanostructure of FIG. 2A.

FIG. 3 is a perspective view of a nanowire which may be employed in a biosensor according to example embodiments. Referring to FIG. 3, a nanowire 110 of a single crystalline phase may be grown. The growth length of the nanowire 110 may be longer than the length of the active area AR such that the nanowire 110 may function as a channel in each active area AR even when the nanowire 110 is partly removed or patterned during a subsequent etching process. For example, the nanowire 110 may be grown to be about ten times longer than the length of the active area AR.

A coating film 120 may be formed on the nanowire 110. The formation of the coating film 120 may be performed in-situ after the growth of the nanowire 110. The coating film 120 may function to help stabilize and/or protect the nanowire 110. A variety of layers having a predetermined thickness and a predetermined strength may be used as the coating film 120 to achieve the stability and/or protection of the nanowire 110. The coating film 120 may also function to help reduce or prevent electrical communication between adjacent nanowires 110 in directions other than a channel direction. Additionally, the coating film 120 may function as an activation layer to help couple linkers and/or probes to the nanowire 110. To function as an activation layer, the coating film 120 may be made of a material containing functional groups capable of coupling with the linkers and/or probes. Furthermore, the coating film 120 may function as a gate insulating film.

The coating film 120 may be made of an insulating material such that electrical communication between adjacent nanowires 110 may be reduced or prevented. As a result, relatively efficient electrical communication in a channel direction may be achieved. When the probe is a DNA oligomer probe (e.g., oligo nucleotide probe), the functional groups capable of coupling with the DNA probe and/or the linker coupled thereto may be hydroxyl groups, aldehyde groups, carboxyl groups, amino groups, amide groups, thiol groups, halo groups, and sulfonate groups. Accordingly, the coating film 120 may be made of a silicon oxide layer (e.g., a plasma enhanced-TEOS (PE-TEOS) layer, a relatively high density plasma (HDP) oxide layer, a P—SiH$_4$ oxide layer, a thermal oxide layer); a silicate (e.g., hafnium silicate, zirconium silicate); a metal oxynitride layer (e.g., a silicon nitride layer, a silicon oxynitride layer, a hafnium oxynitride layer, a zirconium oxynitride layer); a metal oxide layer (e.g., a titanium oxide layer, a tantalum oxide layer, an aluminum oxide layer, a hafnium oxide layer, a zirconium oxide layer, an indium tin oxide (ITO) layer); a polyimide; a polyamine; a metal (e.g., gold, silver, copper, palladium); or a polymer (e.g., polystyrene, polyacrylate, polyvinyl).

To function as a gate insulating film, the coating film 120 may be made of a material having an insulating property. The coating film 120 may be made of a silicon oxide layer or a relatively high dielectric oxide layer, although example embodiments are not limited thereto. For example, the relatively high dielectric oxide layer may be a metal oxide layer. If the coating film 120 is made of a silicon oxide layer or a metal oxide layer, all of the above-described functions may be achieved simultaneously. Thus, for instance, a thermal oxide layer may be formed in-situ as the coating film 120 on the surface of the nanowire 110 after the growth of the nanowire 110. However, it should be understood that example embodiments are not limited to the above examples.

FIGS. 4 through 11 are cross-sectional views of a method of fabricating a biosensor according to example embodiments. A plurality of nanowires 110 may be coated with a coating film 120. The coated nanowires 110 may be disposed on a substrate 100 using a Languir-Blodgett (LB) method or a flow method. The substrate 100 may be made of a material that may be removed by grinding or melting. A material that may be removed by grinding may include a semiconductor wafer substrate or a transparent substrate (e.g., quartz, glass). A material that may be removed by melting may include a plastic substrate. For instance, the plastic substrate may be melted at a relatively high temperature (e.g., about 400° C.). However, it should be understood that the substrate 100 is not limited to the above examples.

The plurality of nanowires 110 may be disposed relatively close to each other and in parallel on the substrate 100, the nanowires 110 extending in the X direction (e.g., FIG. 2A). Alternatively, the plurality of nanowires 110 may be arranged in bundles. When nanoparticles 110P (FIG. 2B) are used instead of the nanowires 110, the nanoparticles 110P may be provided on the substrate 100 and clustered by a suitable method (e.g., a thermal process).

Figure 4:
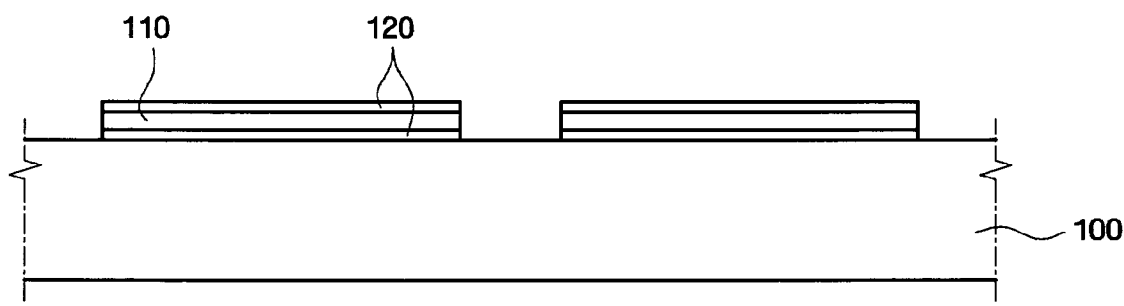
FIGS. 4 through 11 are cross-sectional views of a method of fabricating a biosensor according to example embodiments.

A mask pattern (e.g., a photoresist pattern) may be formed on the substrate 100 to define the active area AR, and the nanowires 110 on the substrate 100 may be etched using the mask pattern as an etching mask. The active area AR may be rectangular shaped, oval shaped, or substantially rectangular with rounded corners. The nanowires 110 may be etched using a dry-etching method. Consequently, as shown in FIG. 4, the plurality of nanowires 110 may remain only in the active area AR. The nanowires 110 may extend in the X direction (e.g., FIG. 2A).

Figure 5:
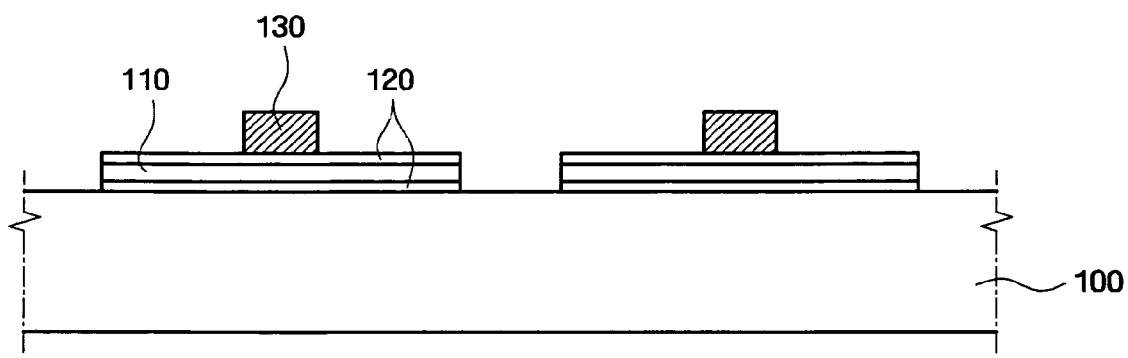

Referring to FIG. 5, gate lines 130 may be formed so as to traverse the active area AR in the Y direction (e.g., FIG. 1). In the area where the gate line 130 intersects the active area AR (the area where the gate line 130 overlaps the nanowires 110), the coating film 120 may act as a gate insulating film that insulates the gate line 130 from the nanowires 110.

Figure 6:
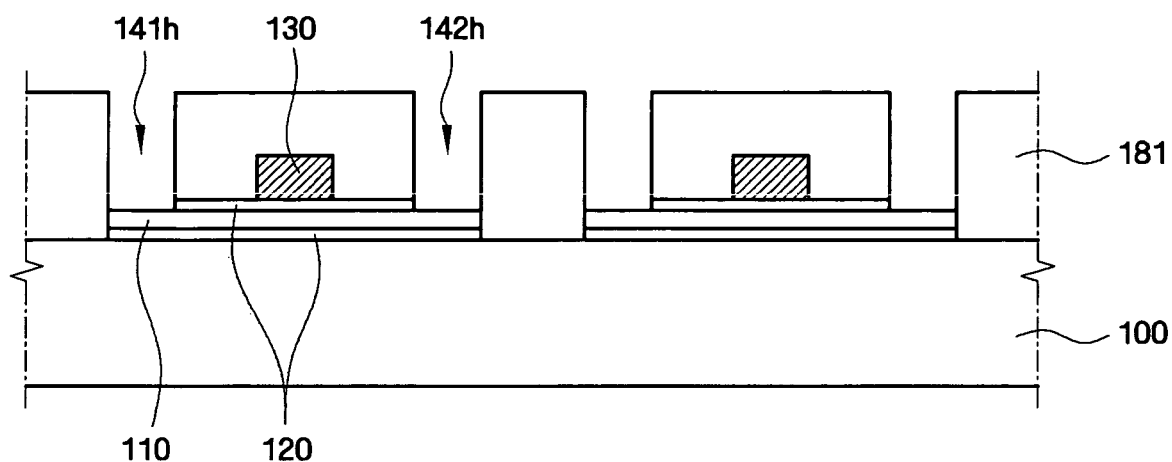

Referring to FIG. 6, a first interlayer insulating film 181 may be formed on the substrate 100. In the interest of restricting the subsequent coupling of probes to the active area AR, it may be beneficial for the first interlayer insulating film 181 to be made of a material (e.g., silicon oxide) which does not contain functional groups capable of coupling with the linkers and/or probes.

A patterning process may be performed on the first interlayer insulating film 181 to expose the first and second ends of each nanowire 110. The patterning process may be performed using dry-etching. A first open area 141h and a second open area 142h may be formed to expose the first and second sides, respectively, of every nanowire 110 along the Y direction (FIG. 1). The coating film 120 in the first and second open areas 141h and 142h may also be removed to expose the nanowires 110. To ensure a relatively secure electrical connection in the Y direction between the first and second signal lines 150 and 160 and the nanowire 110, the first and second open areas 141h and 142h may be formed to extend outwardly in the Y direction from each side of the nanowire 110 by a predetermined margin.

Figure 7:
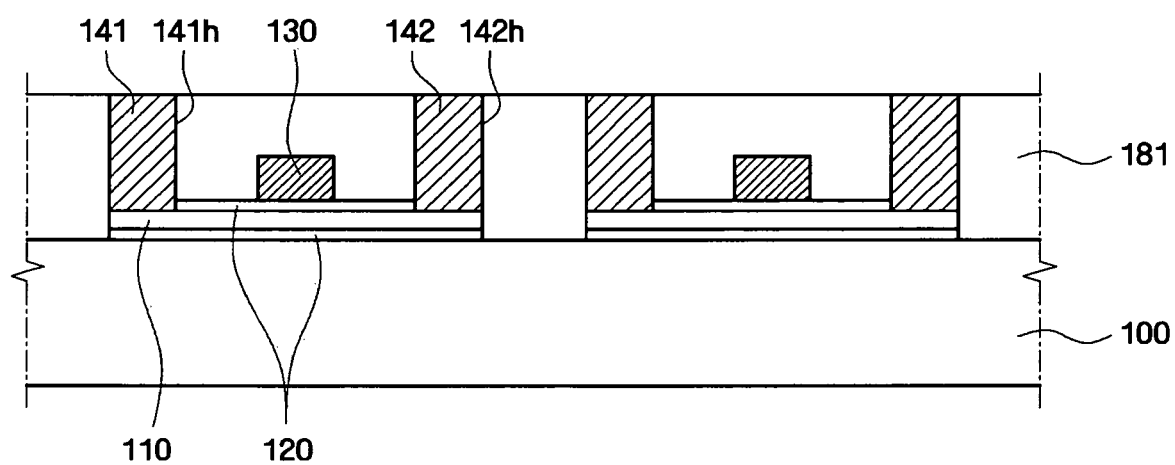

Referring to FIG. 7, the first and second open areas 141h and 142h may be filled with a conductive material to form a first contact pad 141 on a first end of the nanowire 110 and a second contact pad 142 on the second end of the nanowire 110. Consequently, the first and second contact pads 141 and 142 may be electrically connected to the nanowire 110. The first and second contact pads 141 and 142 may cover the width of the active area AR in the Y direction (FIG. 1). It should be noted that, if desired, the first contact pad 141 and the second contact pad 142 may be formed simultaneously with the gate line 130 using a single damascene process.

Figure 8:
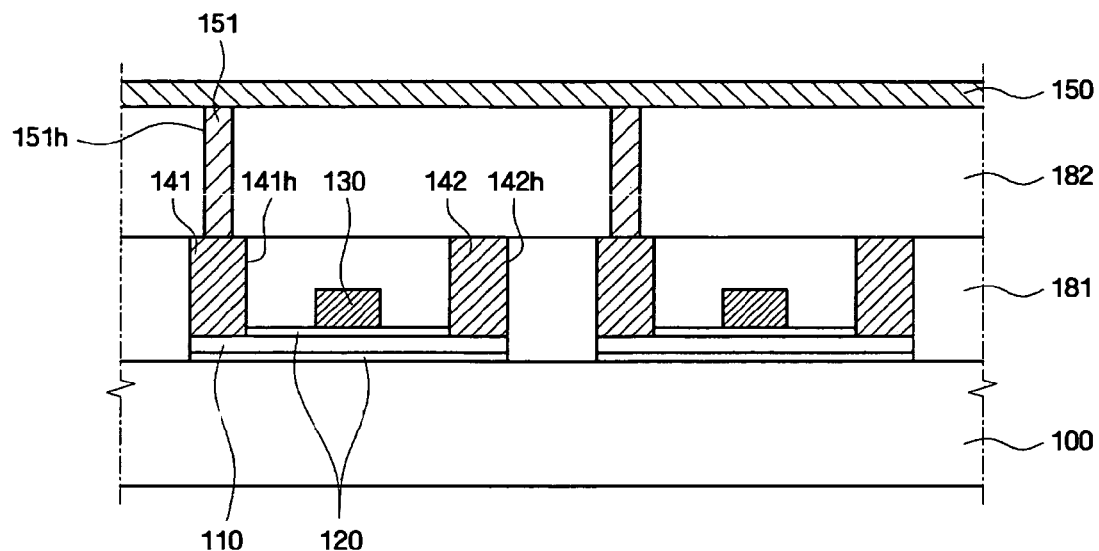

Referring to FIG. 8, a second interlayer insulating film 182 may be formed on the first interlayer insulating film 181. The second interlayer insulating film 182 may be patterned to form a first contact hole 151h to expose the first contact pad 141. The first contact hole 151h may be formed above the center line C (FIG. 1) which divides the active area AR into two regions along the X direction. The first contact hole 151h may be filled with a conductive material to form a first contact 151 that penetrates the second interlayer insulating film 182. The remaining conductive material on the second interlayer insulating film 182 may be laminated and patterned to form the first signal line 150. The first signal line 150 may contact the first contact 151 and extend in the X direction. The first signal line 150 may also have a width that is less than the upper half of the active area AR above the center line C (FIG. 1). The first signal line 150 may be electrically connected to the first end of the nanowires 110 disposed in the active area AR via the first contact 151 and the first contact pad 141.

Figure 9:
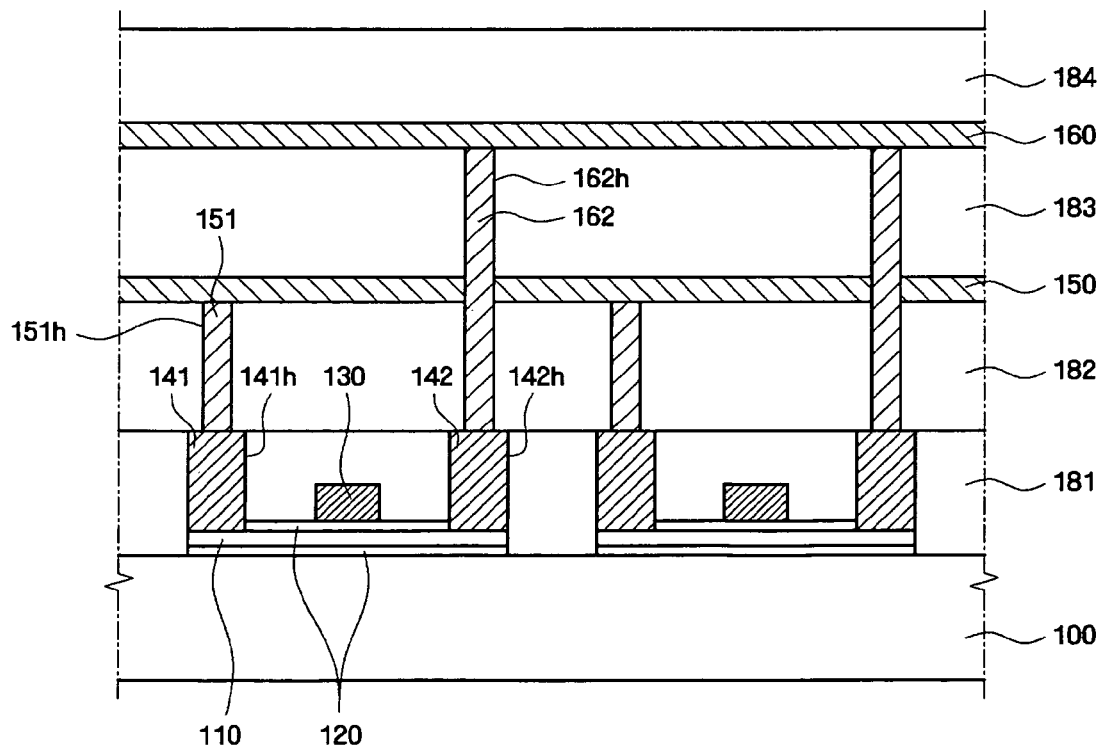

Referring to FIG. 9, a third interlayer insulating film 183 may be formed on the first signal line 150. The third interlayer insulating film 183 and the second interlayer insulating film 182 may be patterned to form a second contact hole 162h to expose the second contact pad 142. To avoid exposing the first signal line 150, the second contact hole 162h may be formed in the lower half of the active area AR below the center line C (FIG. 1). The second contact hole 162h may be filled with a conductive material to form a second contact 162 that penetrates the third interlayer insulating film 183 and the second interlayer insulating film 182. The remaining conductive material may be laminated and patterned to form the second signal line 160. The second signal line 160 may contact the second contact 162 and extend in the X direction. The second signal line 160 may also have a width that is less than the lower half of the active area AR below the center line C (FIG. 1). The second signal line 160 may be electrically connected to the second end of the nanowires 110 disposed in the active area AR via the second contact 162 and the second contact pad 142.

Because the second signal line 160 may be formed on a different layer from the first signal line 150, the second and first signal lines 160 and 150 may be insulated from each other by the third interlayer insulating film 183. It should be understood that the first signal line 150 and the second signal line 160 do not overlap each other. Rather, the first signal line 150 and the second signal line 160 may be arranged, for instance, in parallel, as shown in FIG. 1. Consequently, the first contact 151 and the second contact 162 may be placed in different positions. The second signal line 160 and the first signal line 150 may be electrically insulated from each other. A passivation layer 184 may be formed on the second signal line 160. The passivation layer 184 may be formed of an insulating film.

Figure 10:
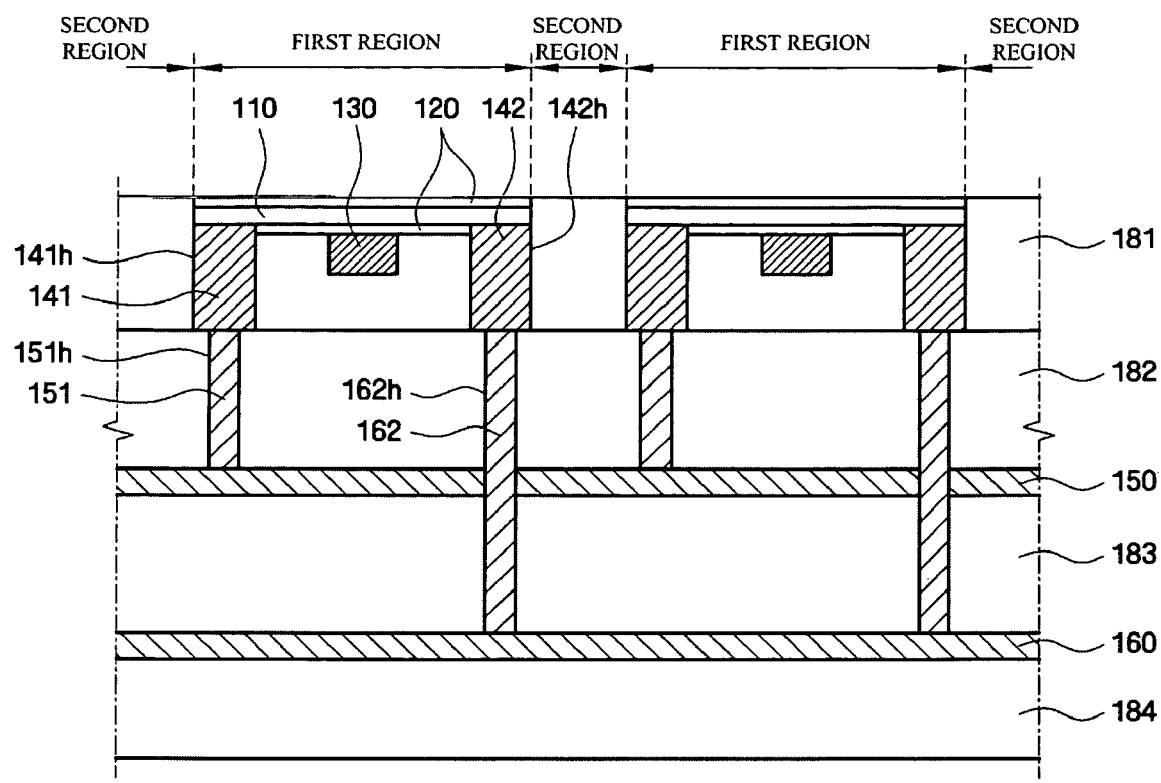

Referring to FIG. 10, the substrate 100 may be removed. Where the substrate 100 is a semiconductor wafer substrate or a transparent substrate (e.g., quartz, glass), the substrate 100 may be removed by grinding. Where the substrate 100 is a plastic substrate, the substrate 100 may be removed by thermal processing at a relatively high temperate. FIG. 10 shows the upside down view of the structure of FIG. 9 after removing the substrate 100. As shown in FIG. 10, a first region may refer to the portion in which the coating film 120 is exposed, and the second region may refer to the portion in which the first interlayer insulating film 181 is exposed. The surface of the first and second regions may be relatively flat. As described above, the coating film 120 may be formed of a material containing functional groups capable of coupling with linkers and/or probes, while the first interlayer insulating film 181 may be formed of a material that does not contain such functional groups. Thus, the first region may refer to the portion that contains the functional groups capable of coupling with linkers and/or probes, while the second region may refer to the portion that does not contain such functional groups. Accordingly, the first region may be an area where probe cells are formed, while the second region may be an area where cell divisions are formed to define the probe cells.

Figure 11:
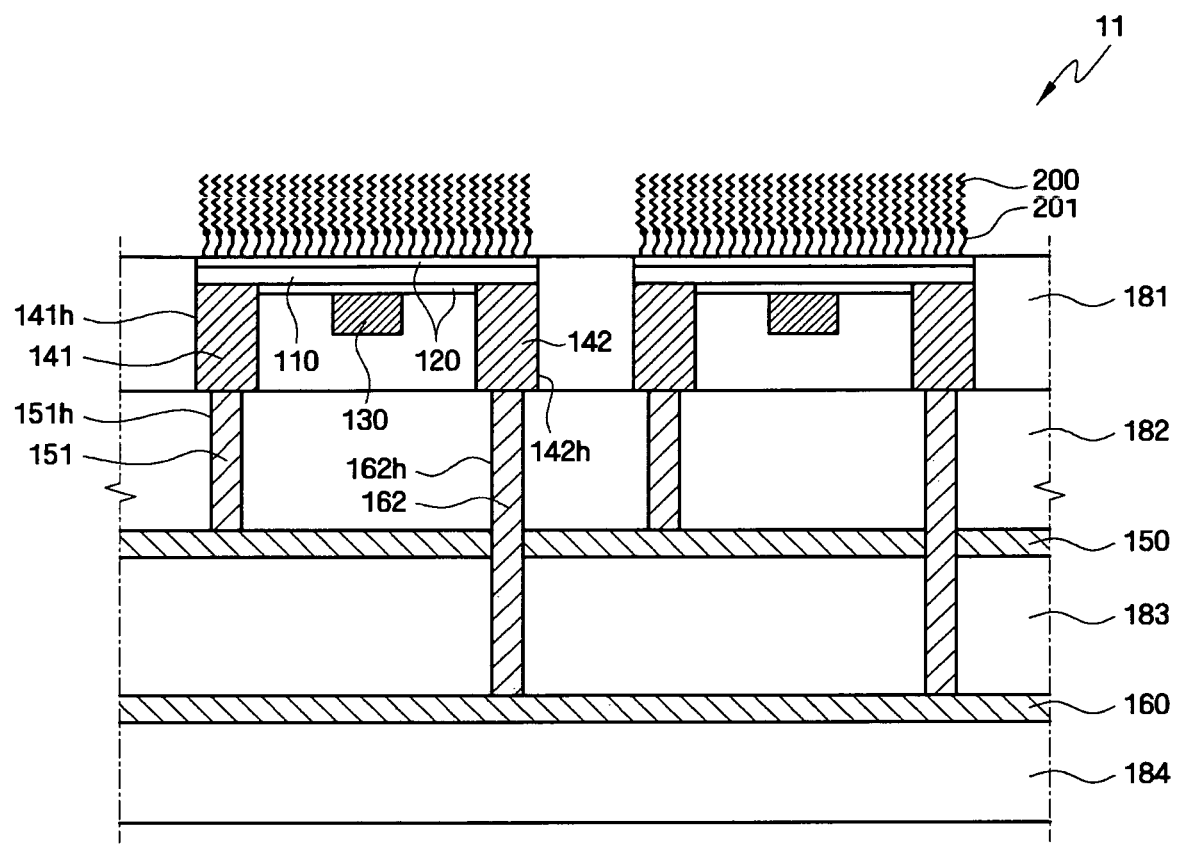

Referring to FIG. 11, the exposed coating film 120 of the first region (FIG. 10) may be selectively coupled with linkers 201 and probes 200 to achieve a biosensor 11 according to example embodiments. Alternatively, the probes 200 may be directly coupled to the coating film 120 or nanowire 110. Before the coupling process, a surface treatment (e.g., ozonolysis, acid treatment, base treatment) may be performed on the surface of the coating film 120 to facilitate the reaction of the coating film 120 with the linkers 201 and/or probes 200. For example, a Piranha solution may be used for the surface treatment, wherein a Piranha solution may be attained by mixing sulfuric acid with hydrogen peroxide, hydrofluoric acid, ammonium hydroxide, or $O_2$ plasma.

The coupling between the linkers 201 and the probes 200 may be carried out using a standard photolithography technique. For example, the linker 201 may be protected with a photolabile group (not shown) and coupled with the coating film 120. The active area AR may be selectively exposed to light to remove the photolabile group. A probe 200 may be protected with a photolabile group and synthesized with the linker 201 on the exposed active area AR. The same or similar process may be repeated for other active areas AR to synthesize probes having different sequences. It should be understood that the coupling of the linkers 201 and/or probes 200 may be carried out using a variety of standard methods. Furthermore, as noted above, the linkers 201 may be omitted, and the probes 200 may be directly coupled with the coating film 120 or nanowire 110.

The biosensor 11 in FIG. 11 may use an insulating film as a base. The insulation film may include the first interlayer insulating film 181, the second interlayer insulating film 182, the third interlayer insulating film 183, and the passivation layer 184. The first signal line 150 may be interposed between the second and third interlayer insulating films 182 and 183. The second signal line 160 may be interposed between the third interlayer insulating film 183 and the passivation layer 184. The nanowires 110 may be disposed on the first interlayer insulating film 181. For instance, the nanowire 110 and the coating film 120 may be positioned in a recessed portion of the first interlayer insulating film 181. A plurality of probes 200 may be coupled to each nanowire 110.

Figure 12:
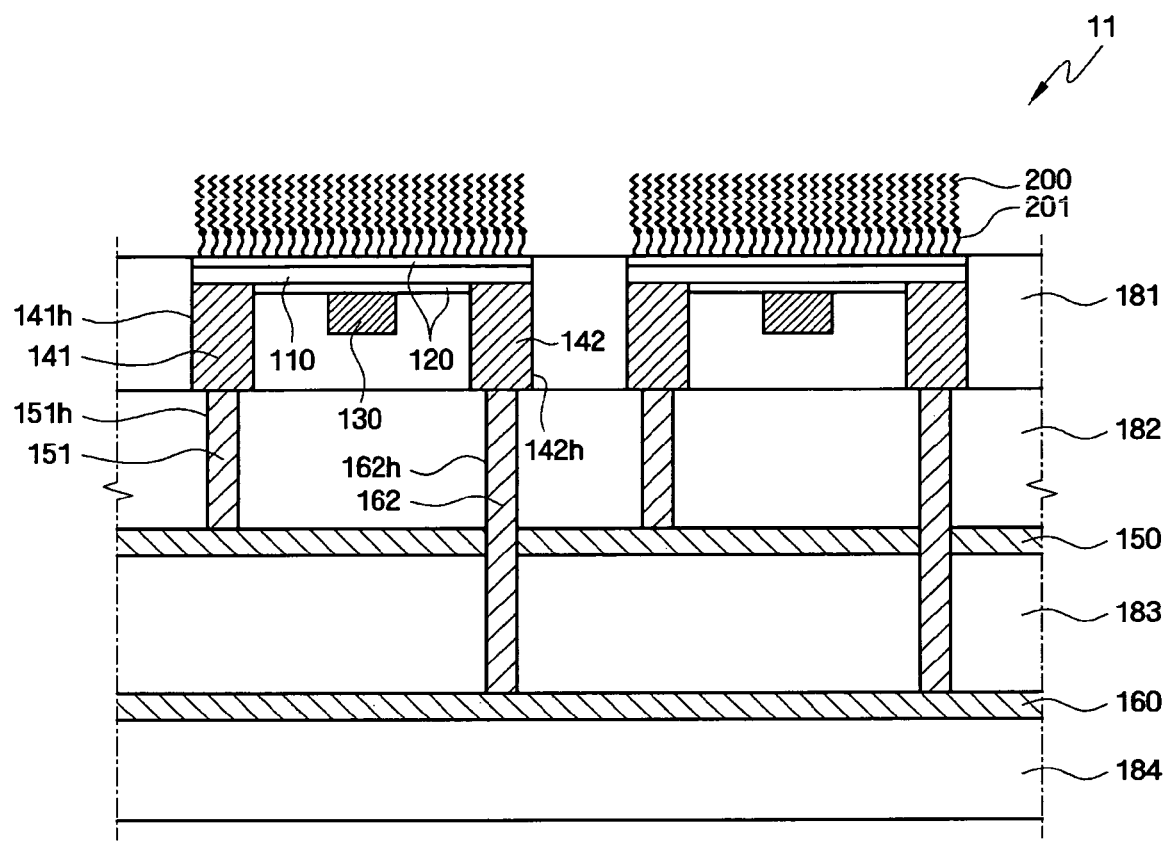
FIGS. 12 through 16 are cross-sectional views of biosensors according to example embodiments.
Figure 13:
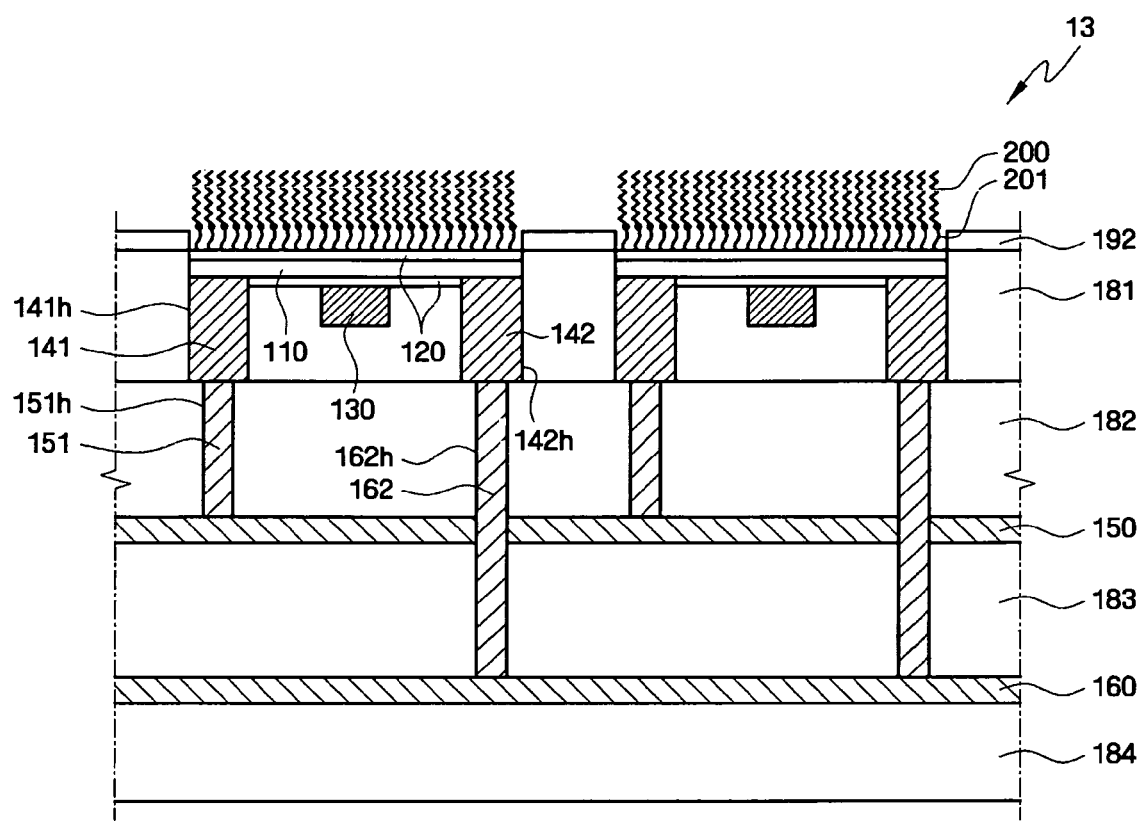

FIGS. 12 to 16 are cross-sectional views of biosensors according to example embodiments. FIG. 12 illustrates a biosensor 11 fabricated according to the method of FIGS. 4-11. Referring to FIG. 13, the biosensor 13 may include a capping layer pattern 192 on the first interlayer insulating film 181. The capping layer pattern 192 may be made of a material that does not contain functional groups capable of coupling with the linkers 201 and/or probes 200. The capping layer pattern 192 may be beneficial in situations where the first interlayer insulating film 181 contains at least a few functional groups capable of coupling with the linkers 201 and/or probes 200. Consequently, the capping layer pattern 192 may reduce or prevent coupling noise caused by the unintended coupling of linkers 201 and/or probes 200 to the first interlayer insulating film 181. The capping layer pattern 192 may be attained by forming a capping layer on the entire surface of the first interlayer insulating film 181 and the coating film 120. The capping layer may be patterned to expose the coating film 120 (e.g., the first region of FIG. 10) while remaining on the first interlayer insulating film 181 (e.g., the second region of FIG. 10).

Figure 14:
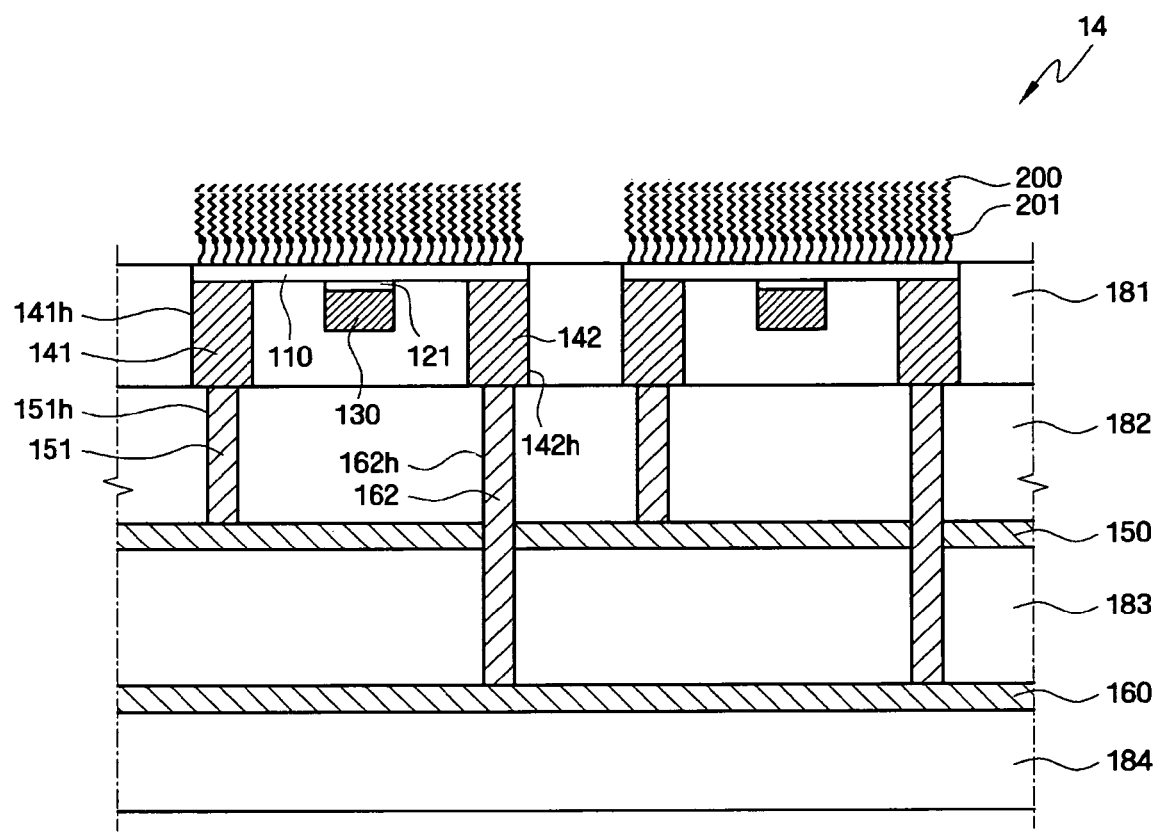

Referring to FIG. 14, the biosensor 14 may omit the coating film on the nanowire 110. Instead, a gate insulating film 121 may intervene between the nanowire 110 and the gate line 130 for purposes of insulation. The gate insulating film 121 may have substantially the same pattern as the gate line 130. When the nanowire 110 contains functional groups capable of coupling with the linker 201 and/or probes 200, the probes 200 may be directly coupled (not shown) to the nanowire 110 or indirectly coupled to the nanowire 110 via the linkers 201, as shown in FIG. 14. On the other hand, when the nanowire 110 does not contain functional groups capable of coupling with the linkers 201 and/or probes 200, a surface activation layer 191 may be formed on the nanowire 110, as shown in FIG. 15.

Figure 15:
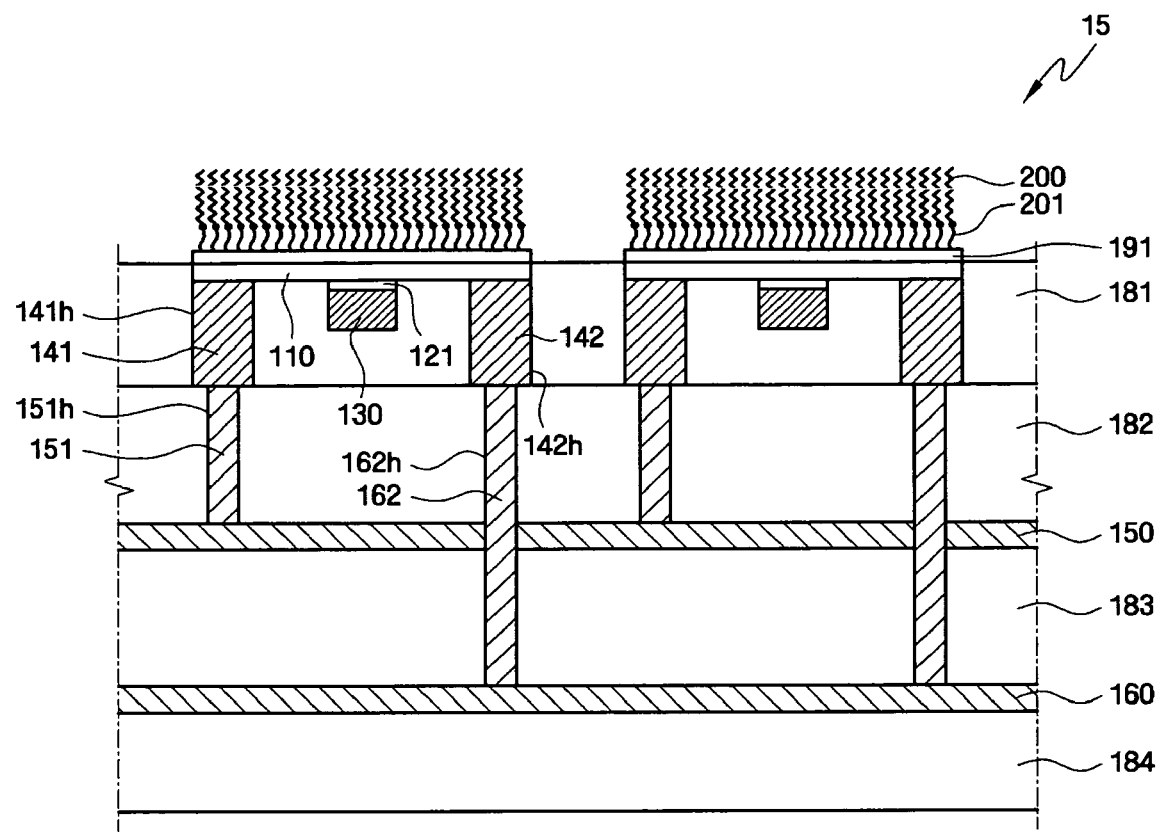

Referring to FIG. 15, the biosensor 15 may include a surface activation layer 191 on the nanowire 110. The surface activation layer 191 may be formed of a material containing a functional group capable of coupling with the linkers 201 and/or probes 200. The surface activation layer 191 may be beneficial in situations where the nanowire 110 (or coating film 120) does not contain functional groups capable of coupling with the linkers 201 and/or probes 200 or contains an insufficient number of functional groups for satisfactory coupling. Formation of the surface activation layer 191 on the nanowire 110 (or coating film 120) may be performed by selectively laminating the surface activation layer 191 based on the difference between the material constituting the coating film 120 and the material constituting the first interlayer insulating film 181. Alternatively, the surface activation layer 191 may be attained by forming an activation layer on the entire surface of the first interlayer insulating film 181 and patterning the activation layer to form the surface activation layer 191.

Figure 16:
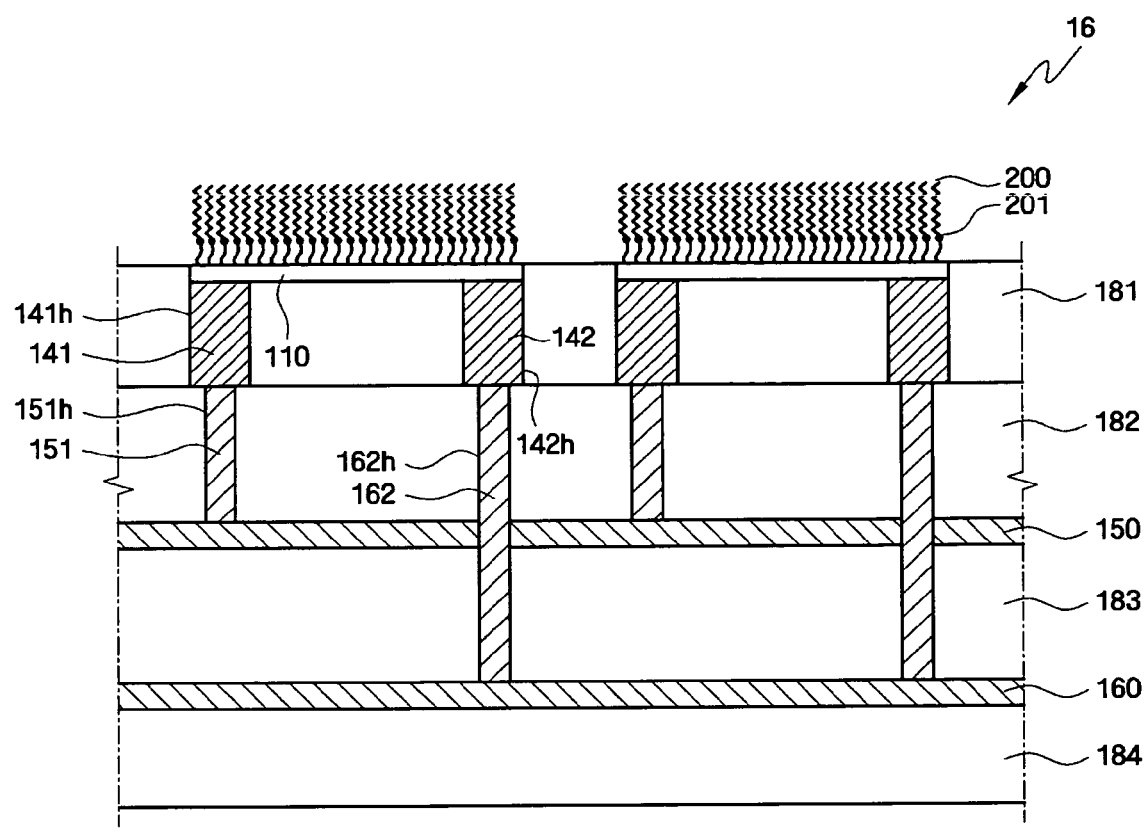

Referring to FIG. 16, the biosensor 16 may omit the gate line. When the gate line is omitted, a gate insulating film may not be necessary. The coating film may also be omitted. Consequently, the probes 200 may be coupled to the nanowire 110 through the linkers 201 in the absence of an intervening layer. However, as described above, a coating film or surface activation layer may be additionally formed on the nanowire 110. Furthermore, it should be noted that various combinations of the above examples may be achieved according to example embodiments.

While example embodiments have been disclosed herein, it should be understood that other variations may be possible. Such variations are not to be regarded as a departure from the spirit and scope of example embodiments of the present disclosure, and all such modifications as would be obvious to one skilled in the art are intended to be included within the scope of the following claims.

The invention claimed is:

1. A biosensor comprising:
  a plurality of insulating films;
  a first signal line and a second signal line between the plurality of insulating films;
  a semiconductor nanostructure on the plurality of insulating films, the semiconductor nanostructure having a first side electrically connected to the first signal line and a second side electrically connected to the second signal line; and
  a plurality of probes coupled to the semiconductor nanostructure,
  wherein the biosensor includes a first region and a second region,
  the semiconductor nanostructure is in the first region,
  the plurality of insulating films include an uppermost insulating film, and
  an upper surface of the semiconductor nanostructure in the first region and an upper surface of the uppermost insulating film in the second region are relatively flat.

2. The biosensor of claim 1, wherein the plurality of insulating films includes an outer insulating film having an outer surface with a recess region, the semiconductor nanostructure being disposed in the recess region.

3. The biosensor of claim 1, wherein the plurality of insulating films includes more than two interlayer insulating films, the first and second signal lines being insulated from each other by at least one interlayer insulating film.

4. The biosensor of claim 1, further comprising:
  a gate line insulated from the semiconductor nanostructure, the gate line traversing the first and second signal lines.

5. The biosensor of claim 1, further comprising:
  a coating film on the semiconductor nanostructure.

6. The biosensor of claim 1, further comprising:
  a surface activation layer on the semiconductor nanostructure.

7. The biosensor of claim 1, wherein the semiconductor nanostructure includes at least one of a nanowire structure, a nanotube structure, and a nanoparticle structure.

8. The biosensor of claim 1, wherein the semiconductor nanostructure includes at least one of Si, ZnO, GaN, Ge, InAs, GaAs, and C.

9. The biosensor of claim 1, wherein the semiconductor nanostructure is a multi-walled nanostructure having a core and at least one shell surrounding the core.

10. The biosensor of claim 1, wherein the upper surface of the semiconductor nanostructure in the first region and the upper surface of the uppermost insulating film in the second region are at about a same level.

11. A biosensor comprising:
  a plurality of insulating films including more than two interlayer insulating films;
  a first signal line and a second signal line between the plurality of insulating films, the first and second lines being insulated from each other by at least one interlayer insulating film;
  a semiconductor nanostructure on the plurality of insulating films, the semiconductor nanostructure having a first side electrically connected to the first signal line and a second side electrically connected to the second signal line;
  a plurality of probes coupled to the semiconductor nanostructure;
  a first contact penetrating at least one of the more than two interlayer insulating films to electrically connect the first signal line with the first side of the semiconductor nanostructure; and
  a second contact penetrating at least two of the more than two interlayer insulating films to electrically connect the second signal line with the second side of the semiconductor nanostructure.

12. The biosensor of claim 11, further comprising:
  a first contact pad connecting the first contact with the first side of the semiconductor nanostructure, the first contact pad having a width larger than a width of the first contact; and a second contact pad connecting the second contact with the second side of the semiconductor nanostructure, the second contact pad having a width larger than a width of the second contact.

13. A method of fabricating a biosensor, comprising:

disposing a semiconductor nanostructure on a substrate;

forming a plurality of insulating films, a first signal line, and a second signal line on the semiconductor nanostructure, the first signal line being electrically connected to a first side of the semiconductor nanostructure and the second signal line being electrically connected to a second side of the semiconductor nanostructure;

exposing the semiconductor nanostructure by removing the substrate; and coupling a plurality of probes to the semiconductor nanostructure.

14. The method of claim 13, wherein removing the substrate includes grinding or melting the substrate.

15. The method of claim 13, wherein forming the plurality of insulating films, the first signal line, and the second signal line includes forming a lower interlayer insulating film on the semiconductor nanostructure, forming the first signal line on the lower interlayer insulating film, forming an upper interlayer insulating film on the first signal line, and forming the second signal line on the upper interlayer insulating film.

16. The method of claim 13, further comprising:

forming a gate line insulated from the semiconductor nanostructure, the gate line traversing the first and second signal lines.

17. The method of claim 13, further comprising:

providing a coating film on the semiconductor nanostructure.

18. The method of claim 13, wherein the semiconductor nanostructure includes at least one of a nanowire structure, a nanotube structure, and a nanoparticle structure.

19. The method of claim 13, wherein the semiconductor nanostructure includes at least one of Si, ZnO, GaN, Ge, InAs, GaAs, and C.

20. The method of claim 13, wherein the semiconductor nanostructure is a multi-walled nanostructure having a core and at least one shell surrounding the core.

21. The method of claim 15, further comprising:

forming a first contact penetrating the lower interlayer insulating film to electrically connect the first signal line with the first side of the semiconductor nanostructure, and forming a second contact penetrating the lower and upper interlayer insulating films to electrically connect the second signal line with the second side of the semiconductor nanostructure.

* * * * *